United States Patent
Gao et al.

(10) Patent No.: US 9,751,083 B2
(45) Date of Patent: Sep. 5, 2017

(54) ELECTRONIC MODULE FOR REAL-TIME DROPLET-POSITION SENSING AND DRIVING IN DIGITAL MICROFLUIDIC SYSTEM

(71) Applicant: University of Macau, Macau (CN)

(72) Inventors: Jie Gao, Macau (CN); Tianlan Chen, Macau (CN); Cheng Dong, Macau (CN); Yanwei Jia, Macau (CN); Pui-In Mak, Macau (CN); Mang-I Vai, Macau (CN); Rui Paulo da Silva Martins, Macau (CN)

(73) Assignee: UNIVERSITY OF MACAU, Macau (CN)

( * ) Notice: Subject to any disclaimer, the term of this patent is extended or adjusted under 35 U.S.C. 154(b) by 267 days.

(21) Appl. No.: 14/680,671

(22) Filed: Apr. 7, 2015

(65) Prior Publication Data
US 2016/0296935 A1   Oct. 13, 2016

(51) Int. Cl.
*G01N 27/27* (2006.01)
*B01L 3/00* (2006.01)
*G01N 27/447* (2006.01)

(52) U.S. Cl.
CPC .. *B01L 3/502792* (2013.01); *G01N 27/44704* (2013.01); *G01N 27/44756* (2013.01); *G01N 27/44791* (2013.01); *B01L 2200/143* (2013.01); *B01L 2300/025* (2013.01); *B01L 2300/0887* (2013.01); *B01L 2400/0427* (2013.01)

(58) Field of Classification Search
CPC ....... B01L 3/502792; B01L 2300/0887; B01L 2300/025; B01L 2200/143; B01L 2400/0427; G01N 27/44704; G01N 27/44756; G01N 27/44791
See application file for complete search history.

(56) References Cited

PUBLICATIONS

Murran et al., Capacitance based droplet position estimator for digital microfluidic devices, (2012), Lab Chip, 12, pp. 2053-2059.*
Abdelgawad M, Watson MWL, Wheeler AR, "Hybrid microfluidics: a digital-to-channel interface for in-line sample processing and chemical separations", Lab on a Chip, Issue 8, 2009, 9, pp. 1046-1051.

(Continued)

*Primary Examiner* — Arun S Phasge
(74) *Attorney, Agent, or Firm* — Bacon & Thomas, PLLC

(57) ABSTRACT

According to one aspect of the present disclosure, a digital microfluidic system is provided. The digital microfluidic system includes a device, a control electronics, a field programmed gate array (FPGA), and a computer. The device includes a droplet on an electrode array, where the electrode array includes a plurality of electrodes. The control electronics connects to the device and provides an actuation pulse to the electrodes, where the control electronics generates a capacitance-derived frequency signal. The FPGA connects to the control electronics and collects the capacitance-derived frequency signal. The computer connects to the FPGA, the computer uses a frequency of the capacitance-derived frequency signal to calculate a precise droplet position and generates a duration voltage signal.

14 Claims, 14 Drawing Sheets

(56) References Cited

PUBLICATIONS

Barbulovic-Nad I, Yang H, Park PS, Wheeler AR, "Digital microfluidics for cell-based assays", Lab on a Chip, Issue 4, 2008, pp. 519-526.
Basu AS, "Droplet morphometry and velocimetry (DMV): a video processing software for time-resolved, label-free tracking of droplet parameters", Lab on a Chip, Issue 10, 2013, pp. 1892-1901.
Bogojevic D, Chamberlain MD, Barbulovic-Nad I, Wheeler AR, "A digital microfluidic method for multiplexed cell-based apoptosis assays", Lab on a Chip, Issue 3, 2012, pp. 627-634.
Chakrabarty K, Fair RB, Zeng J, "Design tools for digital microfluidic biochips: toward functional diversification and more than moore", IEEE Transactions on Computer-Aided Design of Integrated Circuits and Systems, vol. 29, Issue 7, pp. 1001-1017.
Chang YH, Lee GB, Huang FC, Chen YY, Lin JL, "Integrated polymerase chain reaction chips utilizing digital microfluidics", Biomedical Microdevices, Sep. 2006, vol. 8, Issue 3, pp. 215-225.
Chen T, Dong C, Gao J, Jia Y, Mak PI, Vai MI, Martins RP, "Natural discharge after pulse and cooperative electrodes to enhance droplet velocity in digital microfluidics", Apr. 23, 2014, AIP Advances, vol. 4, No. 4.
Cho SK, Moon HJ, Kim CJ, "Creating, transporting, cutting, and merging liquid droplets by electrowetting-based actuation for digital microfluidic circuits", Journal of Microelectromechanical Systems, vol. 12, Issue 1, pp. 70-80.
Fair RB, "Digital microfluidics: is a true lab-on-a-chip possible?", Microfluidics and Nanofluidics, Jun. 2007, vol. 3, Issue 3, pp. 245-281.
Fan SK, Huang PW, Wang TT, Peng YH, "Cross-scale electric manipulations of cells and droplets by frequency-modulated dielectrophoresis and electrowetting", Lab on a Chip, Issue 8, 2008, pp. 1325-1331.
Fobel R, Fobel C, Wheeler AR, "DropBot: An open-source digital microfluidic control system with precise control of electrostatic driving force and instantaneous drop velocity measurement", Applied Physics Letters, vol. 102, Issue 19.
Gao J et al, "An intelligent digital microfluidic system with fuzzy-enhanced feedback for multi-droplet manipulation", Lab on a Chip, Issue 3, 2013, pp. 443-451.
Gong J, Kim CJ, "All-electronic droplet generation on-chip with real-time feedback control for EWOD digital microfluidics", Lab on a Chip, Issue 6, 2008, pp. 898-906.
Jebrail MJ, Wheeler AR, "Digital microfluidic method for protein extraction by precipitation", Analytical Chemistry, Issue 81, vol. 1, pp. 330-335.
Jebrail MJ, Bartsch MS, Patel KD, "Digital microfluidics: a versatile tool for applications in chemistry, biology and medicine", Lab on a Chip, Issue 14, 2012, pp. 2452-2463.
Jia YW, Mak PI, Massey C, Martins RR, Wangh LJ, "Construction of a microfluidic chip, using dried-down reagents, for LATEPCR amplification and detection of single-stranded DNA", Lab on a Chip, Issue 23, 2013, pp. 4635-4641.
Liu YJ, Yao DJ, Lin HC, Chang WY, Chang HY, "DNA ligation of ultramicro volume using an EWOD microfluidic system with coplanar electrodes", Journal of Micromechanics and Microengineering, vol. 18, No. 4.
Malic L, Veres T, Tabrizian M, "Nanostructured digital microfluidics for enhanced surface plasmon resonance imaging", Biosensors and Bioelectronics, vol. 26, Issue 5, Jan. 15, 2011, pp. 2053-2059.
Miller EM, Ng AHC, Uddayasankar U, Wheeler AR, "A digital microfluidic approach to heterogeneous immunoassays", Analytical and Bioanalytical Chemistry, Jan. 2011, vol. 399, Issue 1, pp. 337-345.
Ng AHC, Choi K, Luoma RP, Robinson JM, Wheeler AR, "Digital microfluidic magnetic separation for particle-based immunoassays", Analytical Chemistry, Issue 84, vol. 20, pp. 8805-8812.
Noh JH, Noh J, Kreit E, Heikenfeldb J, Rack PD, "Toward active-matrix lab-on-a-chip: programmable electrofluidic control enabled by arrayed oxide thin film transistors", Lab on a Chip, Issue 2, 2012, pp. 353-360.
Pollack MG, Shenderov AD, Fair RB, "Electrowetting-based actuation of droplets for integrated microfluidics", Lab on a Chip, Issue 2, 2002, pp. 96-101.
Ren H, Fair RB, Pollack MG, Shaughnessy EJ, "Dynamics of electro-wetting droplet transport", Sensors and Actuators B: Chemical, vol. 87, Issue 1, Nov. 15, 2002, pp. 201-206.
Schertzer MJ, Ben-Mrad R, Sullivan PE, "Using capacitance measurements in EWOD devices to identify fluid composition and control droplet mixing",Sensors and Actuators B: Chemical, vol. 145, Issue 1, Mar. 4, 2010, pp. 340-347.
Schertzer MJ, Ben Mrad R, Sullivan PE, "Automated detection of particle concentration and chemical reactions in EWOD devices", Sensors and Actuators B: Chemical, vol. 164, Issue 1, Mar. 31, 2012, pp. 1-6.
Shih SCC, Fobel R, Kumar P, Wheeler AR, A feedback control system for high-fidelity digital microfluidics, Lab on a Chip, Issue 3, 2011, pp. 535-540.
Shih SCC et al, "Dried blood spot analysis by digital microfluidics coupled to nanoelectrospray ionization mass spectrometry", Analytical Chemistry, 2012, 84 (8), pp. 3731-3738.
Shih SCC, Barbulovic-Nad I, Yang XN, Fobel R, Wheeler AR, "Digital microfluidics with impedance sensing for integrated cell culture and analysis", Biosensors and Bioelectronics, vol. 42, Apr. 15, 2013, pp. 314-320.
Sista R et al, "Development of a digital microfluidic platform for point of care testing", Lab on a Chip Issue 12, 2008, pp. 2091-2104.
Srigunapalan S, Eydelnant IA, Simmons CA, Wheeler AR, "A digital microfluidic platform for primary cell culture and analysis", Lab on a Chip, Issue 2, 2012, pp. 369-375.
Todd Thorsen SJM, Quake SR, "Microfluidic large-scale integration", Science, Oct. 18, 2002, vol. 298, No. 5593, pp. 580-584.
Cheng Dong, Tianlan Chen, Jie Gao, Yanwei Jia, Pui-In Mak, Mang-I Vai, Rui P. Martins, "On the droplet velocity and electrode lifetime of digital microfluidics: voltage actuation techniques and comparison", Microfluidics and Nanofluidics, Aug. 19, 2014.
Bhattacharjee & Najjaran. Droplet sensing by measuring the capacitance between coplanar electrodes in a digital microfluidic system. Lab Chip 12: 4416-4423 (2012).†
Murran & Najjaran. Capacitance-based droplet position estimator for digital microfluidic devices. Lab Chip 12: 2053-2059 (2012).†
Gao et al. An intelligent digital microfluidic system with fuzzy-enhanced feedback for multi-droplet manipulation. Lab Chip 13: 443 (2013).†

\* cited by examiner
† cited by third party

Electrode breakdown    Intact electrode

ELECTRONIC MODULE FOR REAL-TIME DROPLET-POSITION SENSING AND DRIVING IN DIGITAL MICROFLUIDIC SYSTEM

BACKGROUND

Field of Invention

The present disclosure relates to an electronic module for real-time sensing and driving. More particularly, the present disclosure relates to an electronic module for real-time droplet-position sensing and driving in digital microfluidic system.

Description of Related Art

In recent years, introduction of electronic automation in digital microfluidics (DMF) systems has intensified them as a prospective platform for managing the intricacy of large-scale micro-reactors that have underpinned a wide variety of chemical/biological applications such as immunoassays, DNA sample processing and cell-based assays. Yet, to further position DMF in high throughput applications like cell sorting and drug screening, the velocity ($v_{droplet}$) of droplet transportation must be improved, without compromising its strong reliability and controllability features. The limitation of a droplet transportation velocity depends on the actuation voltage and the size of a droplet. Empirically it barely reached 2.5 mm/s at an actuation voltage below 20 V.

Under the principle of electrowetting-on-dielectric (EWOD), $v_{droplet}$ is determined by the following parameters: (1) surface roughness and hydrophobicity of the fabricated chip; (2) hydro-dynamics of droplets that can be chemical reagents or biological species with very different compositions; (3) strength of the electric field for surface-tension modulation, and (4) viscous mediums causing drag forces that increase the power required to manipulate the droplets.

A few attempts have been made to address the problems based on hardware. One hardware solution is using the co-planar electrodes as a top-plate-less DMF system to reduce the viscous drag forces between the liquid-solid interfaces. Another hardware solution is using a water-oil core-shell structure to achieve high $v_{droplet}$. The aforementioned hardware solutions are vulnerable to contamination and evaporation that are intolerable for essential applications like polymerase chain reaction (PCR). Another hardware solution is tailoring the electrode shape to boost $v_{droplet}$.

Instead of hardware modification, unguided DC-pulse train could already regulate $v_{droplet}$ let for non-deformed droplet manipulation by adjusting the actuation signal. However, $v_{droplet}$ was lower than that of DC. Another work designated residual charging was capable to execute multi-droplet manipulation, but the waveform parameters were not studied for an optimum $v_{droplet}$.

Naturally, elevating the electrode-driving voltage can raise the electric field to accelerate $v_{droplet}$, but still, compromising the chip lifetime due to dielectric breakdown, and the cost of the electronics which goes up with their voltage affordability. To our knowledge, there is no electrode-driving technique that can concurrently enhance $v_{droplet}$ and elongate electrode lifetime of a DMF chip.

SUMMARY

According to one aspect of the present disclosure, a digital microfluidic system is provided. The digital microfluidic system includes a device, a control electronics, a field programmed gate array (FPGA), and a computer. The device includes a droplet on an electrode array, where the electrode array includes a plurality of electrodes. The control electronics connects to the device and provides an actuation pulse to the electrodes, where the control electronics generates a capacitance-derived frequency signal. The FPGA connects to the control electronics and collects the capacitance-derived frequency signal. The computer connects to the FPGA, the computer uses a frequency of the capacitance-derived frequency signal to calculate a precise droplet position and generates a duration voltage signal.

According to another aspect of the present disclosure, a digital microfluidic system is provided. The digital microfluidic system includes a device, a control electronics, a FPGA, and a computer. The device includes a droplet on an electrode array, where the electrode array includes a first electrode and a second electrode. The control electronics connects to the device and provides a first pulse to the first electrode, where the control electronics generates a capacitance-derived frequency signal. The FPGA connects to the control electronics and collects the capacitance-derived frequency signal. The computer connects to the FPGA, the computer uses a frequency of the capacitance-derived frequency signal to calculate a precise droplet position and generates a duration voltage signal. In which, the control electronics conducts a control process according to the duration voltage signal. The control process includes, the first pulse is provided to the first electrode for kicking off the droplet till a centroid of the droplet reaching a centroid of the first electrode. A second pulse is provided to the second electrode when a leading edge of the droplet reaches the second electrode.

BRIEF DESCRIPTION OF THE DRAWINGS

The present disclosure can be more fully understood by reading the following detailed description, with reference made to the accompanying drawings as follows.

DETAILED DESCRIPTION

Figure 1A:
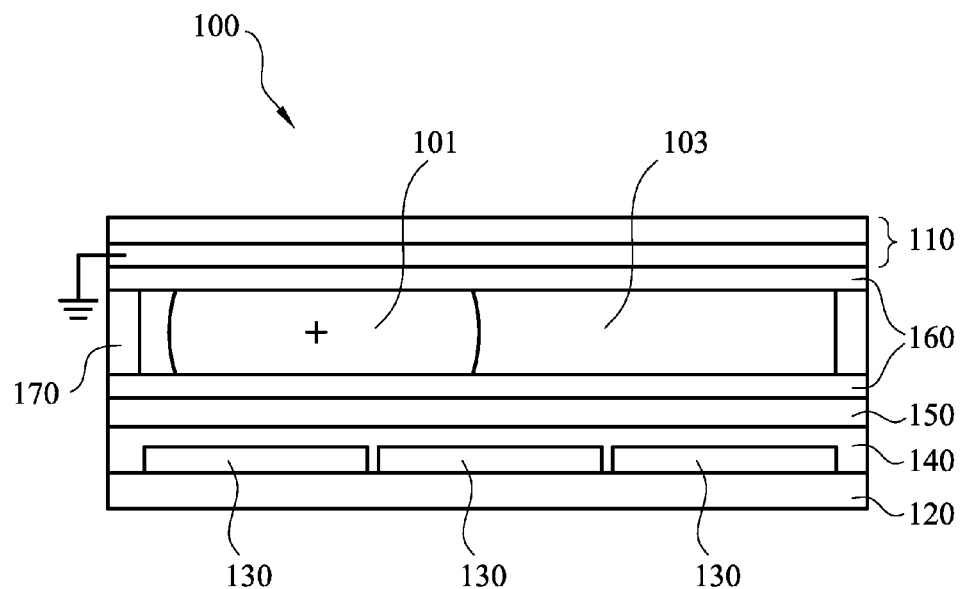
FIG. 1A is a schematic diagram showing an electrowetting-on-dielectric (EWOD) device according to one embodiment of the present disclosure.

FIG. 1A is a schematic diagram showing an electrowetting-on-dielectric (EWOD) device 100 according to one embodiment of the present disclosure. A drop of aqueous solution 101 (~0.5 μL) immersed in silicon oil 103 (1 cSt) (Sigma-Aldrich, MO) or hexadecane (3.34 cSt) (Sigma-Aldrich, MO) was sandwiched by a top Indium Tin Oxide (ITO, Kaivo Optoelectronic) glass 110 and a bottom glass 120 with a 0.25 mm spacer 170. Electrodes 130 (1 mm×1 mm) patterned on the bottom glass 120 are separated from each other with a 0.01 mm gap. A dielectric layer of $Ta_2O_5$ 140 (250/50 nm) was coated on the electrodes followed by a layer of Parylene C 150 (480 nm) (Galxyl) and then a layer of Teflon 160 (100 nm) (DuPont). Silane A 174 (Momentive Performance Materials) was utilized to improve the bonding between the $Ta_2O_5$ and Parylene C layer. The top ITO glass 110 (Kaivo, ITO-P001) was coated with a layer of 100 nm Teflon 160.

Figure 1B:
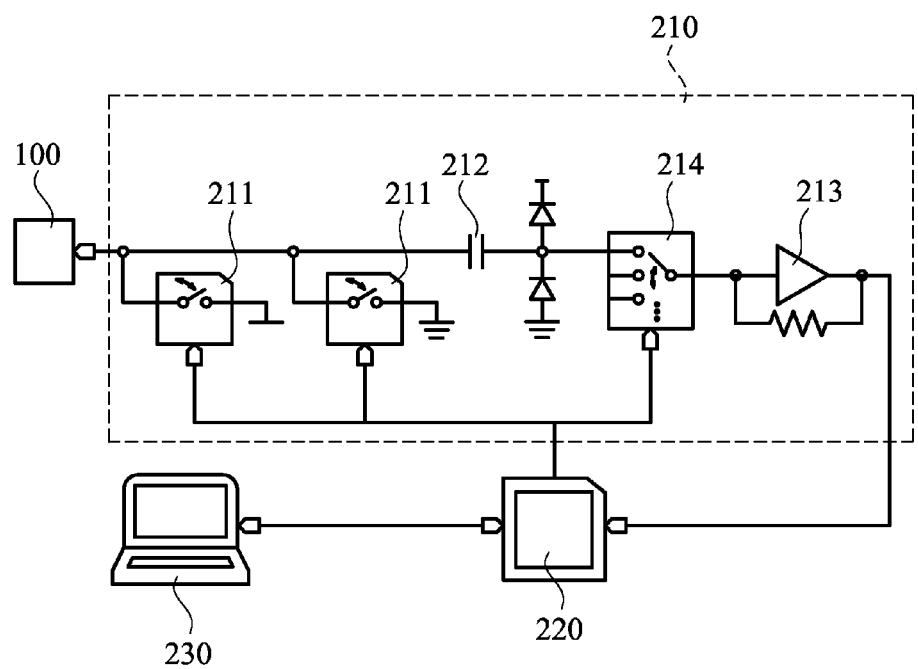
FIG. 1B is a schematic diagram showing an electronic module for real-time droplet position sensing and driving in digital microfluidic system (DMF) according to one embodiment of the present disclosure.

FIG. 1B is a schematic diagram showing an electronic module for real-time droplet position sensing and driving in digital microfluidic (DMF) system according to one embodiment of the present disclosure. The DMF system comprises (FIG. 2): (i) the control electronics 210 (discrete components on printed circuit board, PCB), (ii) the field programmable gate array (FPGA) 220, and (iii) the computer-based software engine 230. The control electronics 210 connects to the EWOD device 100 and provides an actuation pulse to the electrodes, where the control electronics 210 generates a capacitance-derived frequency signal. The FPGA 220 connects to the control electronics 210 and collects the capacitance-derived frequency signal. The computer 230 connects to the FPGA 220, the computer 230 uses a frequency of the capacitance-derived frequency signal to calculate a precise droplet position and generates a duration voltage signal. The control electronics 210 implements Natural Discharge after Pulse (NDAP)/Cooperative Electrodes (CE) under the guide of the FPGA 220. The PCB comprises a high-voltage (HV) switches IC chip array 211, a blocking capacitance array 212, a ring oscillator 213, and an analog switches IC chip array 214. The HV switches IC chip array 211 is for connecting/disconnecting the actuation pulse to the electrodes. The ring oscillator 213 is for generating the capacitance-derived frequency signal. The analog switches IC chip array 214 is for connecting/disconnecting the electrodes to the ring oscillator 213. The blocking capacitance array 212 is for connecting electrodes to the analog switches array 214, and for blocking a HV signal from the actuation pulse to the analog switches array 214.

DC (direct current) and AC (alternating current) are the common voltage waveforms for electrode driving in EWOD-based DMF devices. Present disclosure provides a new control-engaged electrode-driving technique, NDAP, for better $v_{droplet}$ and electrode lifetime of a EWOD device.

Figure 2:
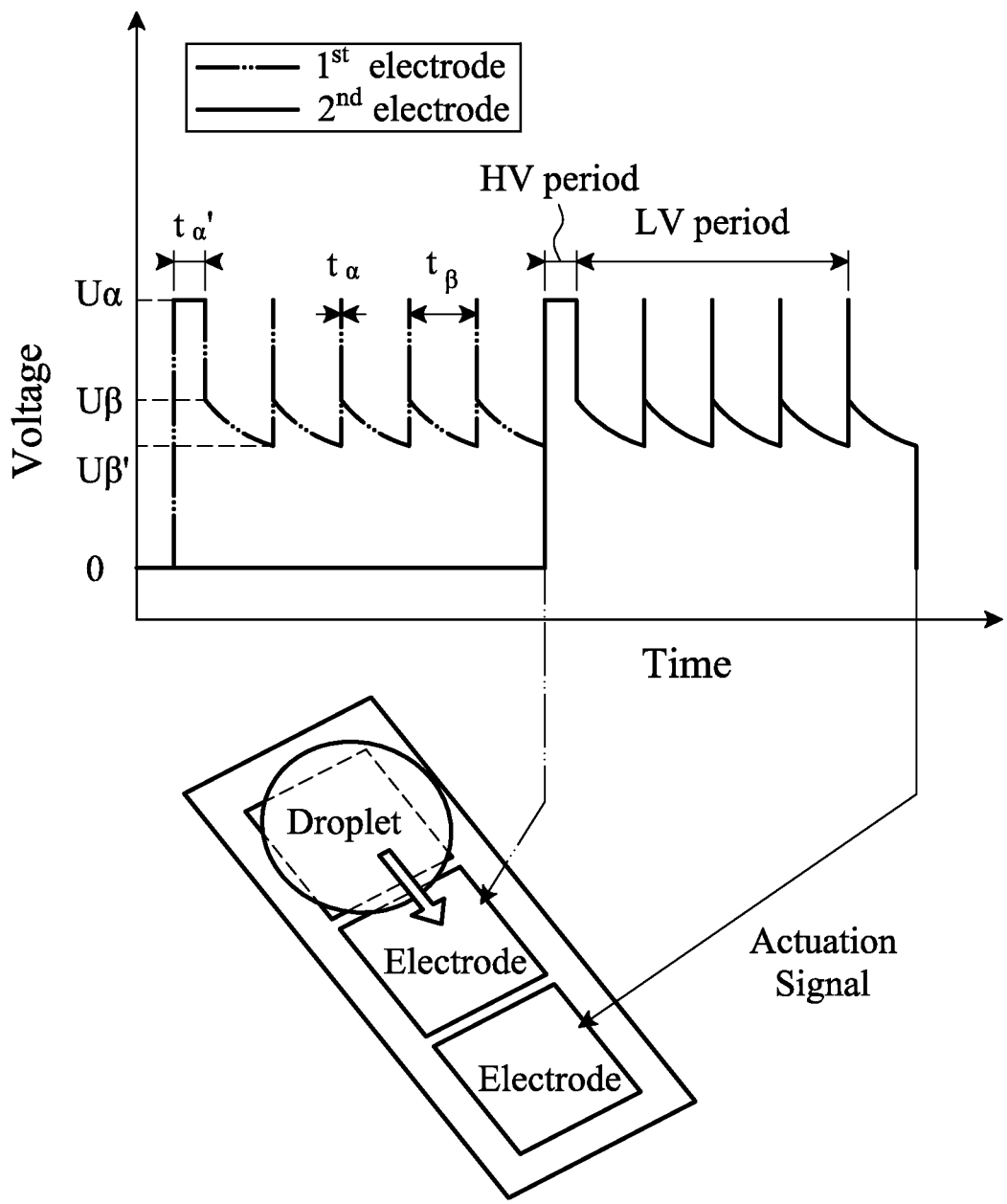
FIG. 2 is a profile showing an electrode-driving signal for a droplet moving across two electrodes according to one embodiment of the present disclosure.

FIG. 2 is a profile showing an electrode-driving signal for a droplet moving across two electrodes according to one embodiment of the present disclosure. As shown in FIG. 2, the initial high-level excitation is a $t'_\alpha$-width DC with a peak value of $u_\alpha$, offering the initial EWOD device force to rapidly accelerate $v_{droplet}$ from still. Before the low-level excitation begins, we allow the high-level excitation to drop to a lower value first, by the operation of the designed circuit described later. When a droplet-in-run starts to move, the high-level excitation will be stopped by disconnecting the electrode from the power source. During the discharge period, the residual charge on the electrode is still adequate for real-time sensing of the dynamic position of the droplet. The corresponding voltage of the residual charge on the electrode ($u_{res}$) is given by $$u_{res} = u_\beta e^{-t/\tau} \quad (1)$$

where $u_\beta$ is the discharge period initial voltage, t is the elapsed time, and $\tau$ is the RC (Resistance-Capacitance) time constant, which is defined as $$\tau = RC \quad (2)$$

During the natural discharge, a number of short (1 ms, $t_\alpha$) recharging pulse is applied to the electrode to sustain $v_{droplet}$ over a longer period $t_\beta$, which can be managed by the control unit that guides the droplet movement till completion. The RMS voltage ($V_{RMS,discharge}$) of discharge period is given by, $$V_{RMS,discharge} = \sqrt{\frac{1}{t_\beta} \int_0^{t_\beta} u_{res}^2 \, dt} \quad (3)$$

Substituting Eqs. (1) and (2) into Eq. (3) yields $$V_{RMS,discharge} = u_\beta \sqrt{\frac{\tau}{2t_\beta}(1 - e^{-2t_\beta/\tau})} \quad (4)$$

which is obviously lower than that during charging. In our case, RMS voltage of the whole excitation is up to 26.7% lower than DC. The NDAP can also be applied to other DMF systems even there is with no position sensing.

The transportation of a droplet from one electrode to another is not linear. The drop transportation between electrodes in three phases: Phase I (only the leading edge moves while the trailing edge is still pinned), Phase II (both the leading and trailing edges move with great different velocities), and Phase III (both edge move in a similar velocity).

Figure 3A:
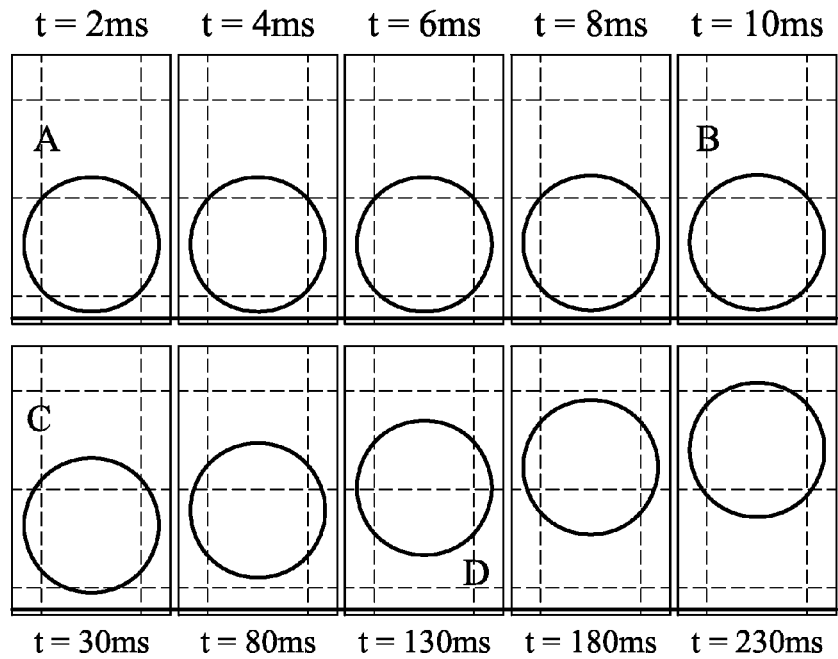
FIG. 3A is an image showing the droplet movement from 0 to 230 ms according to one embodiment of the present disclosure.
Figure 3B:
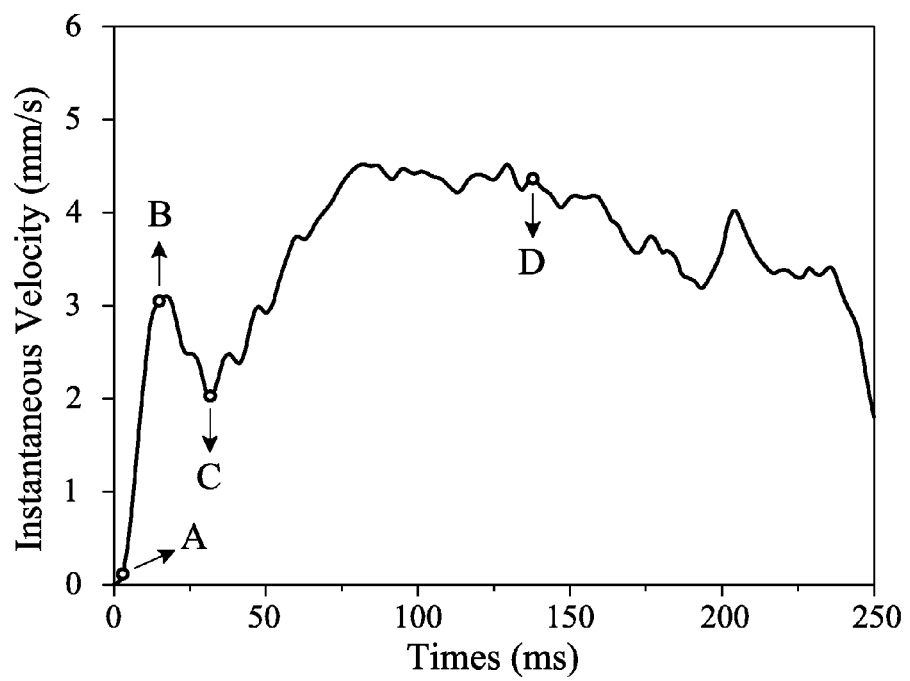
FIG. 3B is a diagram showing instantaneous velocity of a droplet moving across an electrode according to FIG. 3A.

FIG. 3A shows the droplet movement from 0 to 230 ms, where the first row focuses on the very beginning of charging and the second row shows the rest. As soon as the driving signal was applied, Phase I started instantly, resulting a deformation of the droplet shape where the front edge became thinner while the trailing edge stayed pinned. Phase II began at around 10 ms when the trailing edge depinned and started to catch up the leading edge. The present disclosure provides a convenient method to decide the boundary of the three phases from the instantaneous velocity of a droplet, as shown in FIG. 3B. The instantaneous velocity was calculated based on the movement of the droplet centroid, and thus the conformation change of the droplet would be reflected on the velocity. As shown in FIG. 3B, there is a sudden velocity change from 0 to 3 mm/s at the moment when the power is applied. This is due to the deformation of the droplet in Phase I (Frame A in FIG. 3A and point A in FIG. 3B). For the same reason, when the trailing edge started to move, there would be another steep change in the droplet conformation, which would cause a drop in the calculated velocity. Point B at ~10 ms in FIG. 3b marks the beginning of Phase II which is consistent with that obtained from FIG. 3a. When the trailing edge catches up the front edge and keeps the conformation of droplet stable, Phase III starts and the instantaneous velocity would increase smoothly with the continuous driving signal application. Point C in FIG. 3B marks the start of Phase III at around 30 ms. Note that after 130 ms, Point D, the droplet velocity starts to decline. By investigating the video we found that this was the time when the centroid of the droplet reached the lower edge of the target electrode as shown in FIG. 3A. The EWOD force was applied at the contact line. When the centroid of the droplet passed the edge, the EWOD force on the rear part would be a dragging force instead of a driving force which causes the droplet to slow down. There is another sudden velocity change close to the end of the transportation, it happened when the leading edge of the droplet reached the rim of the second electrode and stopped moving forward. Again, the sudden conformation change would be reflected on the velocity. After that, the velocity drops quickly. Hence, by studying the instantaneous velocity of a droplet, we can obtain the dynamics of the droplet transportation, which is crucial in optimizing our NDAP signal as analyzed as follows.

In general, increasing the RMS value of the control signal is an effective way to enhance $v_{droplet}$ on the EWOD device. Nevertheless EWOD device aging and breakdown problems arise while a control voltage with a high RMS voltage is applied. In order to maintain $v_{droplet}$ while lowering the RMS voltage, the efficiency of the control voltage would have to be enhanced.

The present disclosure uses a NDAP signal with a scope of reducing the RMS voltage while improving $v_{droplet}$. To assess the performance of NDAP, we for the first time compared $v_{droplet}$ of DI water driven by NDAP with that driven by DC, for a droplet to move over to the next electrode immersed in silicon oil. The charging time of DC was empirically fixed at 300 ms to complete the transportation. NDAP was executed by the feedback-control unit. The natural discharge can be multi-cycled to complete the overall transportation.

Figure 4A:
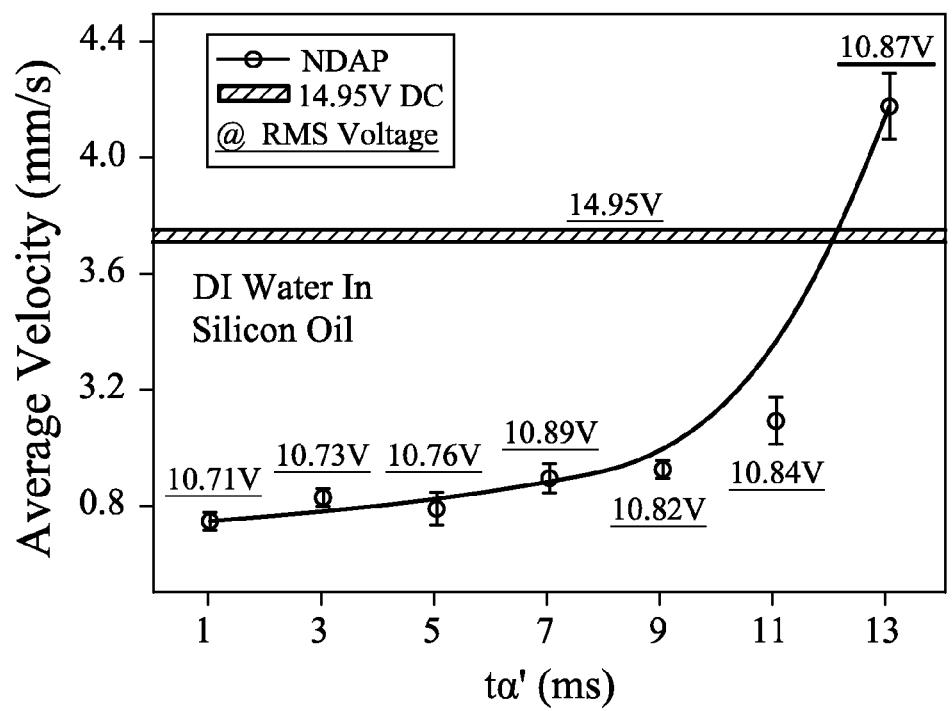
FIG. 4A is a diagram showing the average velocities of a droplet driven by NDAP signals with different $t'_\alpha$ according to one embodiment of the present disclosure.

FIG. 4A is a diagram showing the average velocities of a droplet driven by NDAP signals with different $t'_\alpha$ according to one embodiment of the present disclosure. As illustrated in FIG. 4A, a DC signal with a 15 $V_{RMS}$ gives an average velocity of 3.73 mm/s. This velocity is slightly dependent on the size of the droplet. With the NDAP signal, the average velocity increased dramatically from 2.74 mins with a $t'_\alpha$ of 1 ms, to 4.18 mm/s with a $t'_\alpha$ of 13 ms. The RMS value of 13 ms NDAP was only 10.87 V, 73% of that of DC. However, the average velocity under this condition was even higher than that of the DC driving signal. Considering the droplet dynamics during the transportation, we expected that when the first pulse duration is less than that needed to overcome Phase I, the driving force would be inadequate to move the droplet at a high speed, though the natural discharge in NDAP may still pull the droplet forward. The average transporting efficiency would remain low. However, if the first pulse in NDAP makes the droplet move into Phase II or III, the whole droplet starts to move in a stretching conformation. The retreat of the force would cause the droplet to relax and back to a round shape as much as possible. This rounded shape would maximize the driving force efficiency, which as a consequence enhance the droplet transportation by NDAP even faster than DC due to its high driving efficiency.

Figure 4B:
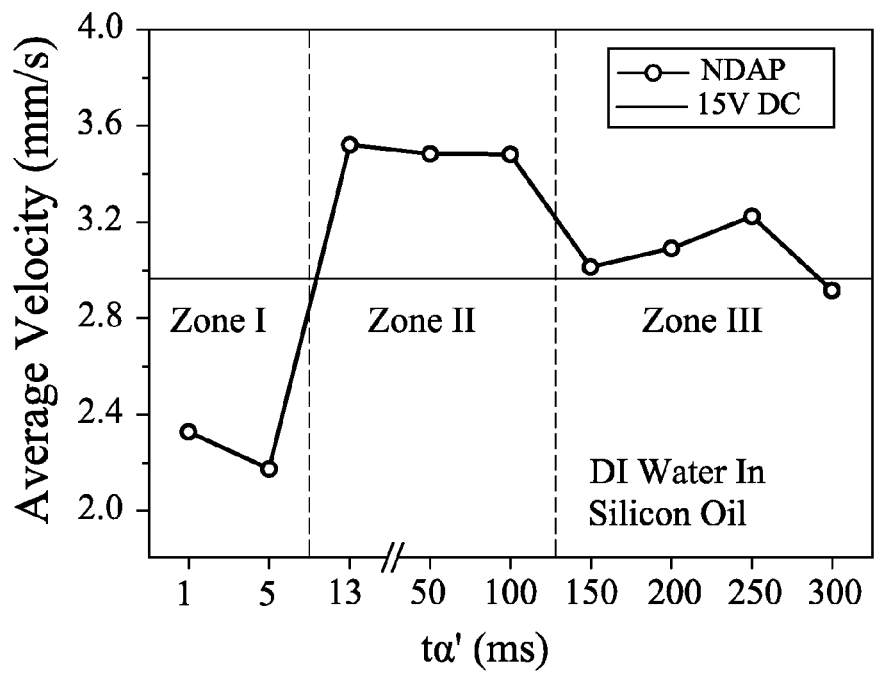
FIG. 4B is a diagram showing the average velocities of a DI droplet in silicon oil driven by NDAP signals with a $t'_\alpha$ changing from 1 to 300 ms according to one embodiment of the present disclosure.

FIG. 4B is a diagram showing the average velocity of droplet transportation with $t'_\alpha$ from 1 to 300 ms. As shown in FIG. 4B, when $t'_\alpha$ is less than 10 ms, which is the boundary of the Phase I and Phase II, the average velocity is less than that driven by DC. This range is labeled as zone I, where the transporting efficiency remains low. However, when $t'_\alpha$ is between 10 ms and 130 ms (zone II), the average velocity reaches ~3.5 mm/s, which is 20.6% higher than that of DC (2.9 mm/s). A further increase of $t'_\alpha$ does not add more benefits. When $t'_\alpha$ is larger than 130 ms (zone III), the velocity returns back to that of DC. As we have discussed, 130 ms is the time when the centroid of the droplet gets onto the second electrode. Under this condition, NDAP shows no more effect because its high driving efficiency works on both the front and trailing edges, which is actually a dragging force. Balancing the velocity and electrode lifetime, we conclude that using a $t'_\alpha$ just into the boundary of Phase II would be the optimized NDAP signal.

The beginning of Phase II may vary with different chemical or biological systems, which would require a calibration for each case. We tested the start point of Phase II with different driving voltages, different immerse oils and different sample components to investigate the variation.

As shown in Table 1, raising $u_\alpha$ from 15 to 25 V shortened the Phase I period from 10 to 7.5 ms for a DI water droplet in silicon oil (1 cSt). Further increase in driving voltage does not affect the phase behavior of the droplet. We also studied the profile for a water droplet dispersed with stabilized 8 μm polysterin particles (Nano Micro. Ltd) to mimic the biological samples with cells in the droplet. The phase behavior stays similar to that of pure deionized water. The beginning of Phase II takes place 2.5 ms earlier with a higher voltage than a just adequate driving voltage.

TABLE 1

Phase II begin time for different conditions

| | Phase II begin time (ms) | | |
|---|---|---|---|
| $u_\alpha$ (V) | DI water in silicon oil (1.0 cSt) | DI water with 8 μm particle in silicon oil (1.0 cSt) | DI water in hexadecane (3.34 cSt) |
| 15 | 10.00 | 10.83 | 15.00 |
| 20 | 8.33 | 8.33 | 12.50 |

TABLE 1-continued

Phase II begin time for different conditions

| $u_\alpha$ (V) | Phase II begin time (ms) | | |
|---|---|---|---|
| | DI water in silicon oil (1.0 cSt) | DI water with 8 μm particle in silicon oil (1.0 cSt) | DI water in hexadecane (3.34 cSt) |
| 25 | 7.50 | 8.33 | 11.67 |
| 30 | 7.50 | 8.33 | 11.67 |
| 35 | 7.50 | 7.50 | 11.67 |

Figure 4C:
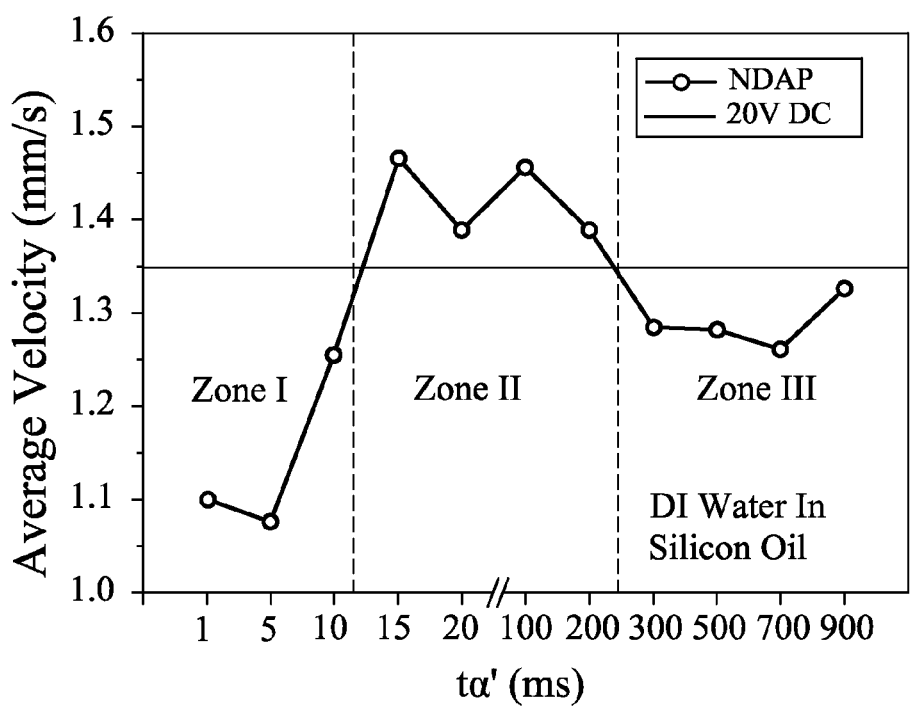
FIG. 4C is a diagram showing the average velocities of a DI droplet in hexadecane driven by NDAP signals with a $t'_\alpha$ changing from 1 to 900 ins according to one embodiment of the present disclosure.

For some biological applications which need heating up the samples, such as PCR, the high evaporation rate of the silicon oil (1 cSt) makes it inappropriate as an immerse oil. Replacing it with thermal stable but more viscous oil is inevitable. We investigated the phase behavior of a water droplet in hexadecane (3.34 cSt) when $u_\alpha$ is equal to 20 V to see if that would cause a necessary recalibration of the system. As shown in Table 1, the Phase II starts at 12.5 ms, which is about 50% later than that in the silicon oil. However, the zone I to zone III for DI water droplet in hexadecane (FIG. 4C) is still consistent with the phenomenon that of in silicon oil, matching its beginning of Phase II (boundary of zone I and II) and centroid time (boundary of zone II and III), which further confirmed our hypothesis.

We admit that the phase behavior of a droplet varies in the range of 4 ms in different immerse oil. However, compared with the range of zone II which is up to 130 ms in silicon oil or 250 ms in hexdecane, the off-optimization of this 4 ms is negligible. Conservatively, one can use the optimized $t'_\alpha$ at a low voltage for all NDAP signals on aqueous droplets. As such, recalibration of the system for different applications is likely unnecessary.

The above comparisons of performance are all between NDAP and DC actuation signals as NDAP is DC-based. In order to further test the performance of our new techniques, we modified our signal generating system and rerun the experiment for the velocity of droplet transportation and electrode lifetime of a EWOD device.

In the experiments of velocity determination, a droplet of DI water (0.5 uL) was transported from one electrode to the next under different actuation signals. The same electrodes were used for alternatively running DC, AC or NDAP. The peak-values of all three signals were fixed at 15 V. In NDAP signal, 15 ms $t_\alpha'$ was used for the best driving performance. The charging of AC or DC was sustained till the movement was completed. Therefore, the RMS voltages of AC, DC and NDAP were 15 V, 15 V and 11.27 V, respectively. The frequency of the AC signal was set at 1 kHz.

Figure 5A:
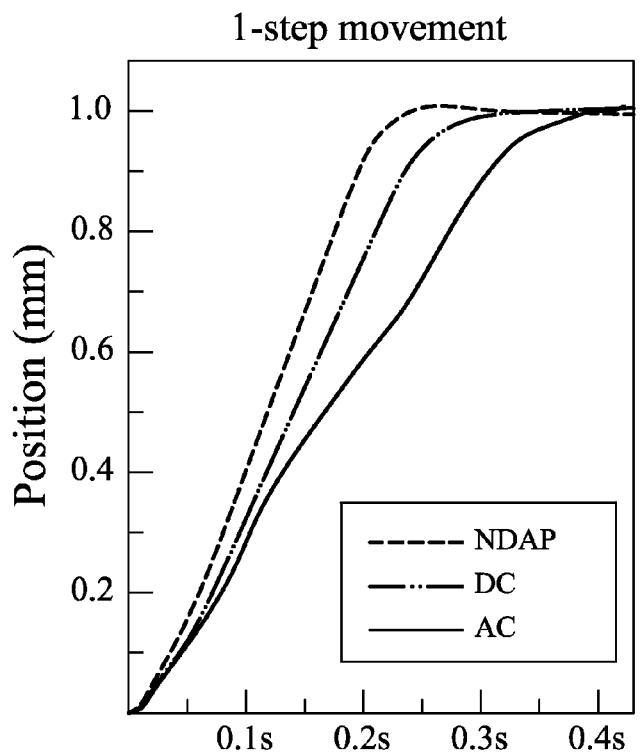
FIG. 5A is a diagram showing velocity comparisons of three different actuation signals according to one embodiment of the present disclosure.

FIG. 5A is a diagram showing velocity comparisons of three different actuation signals according to one embodiment of the present disclosure. As shown in FIG. 5A, the droplet actuated by the NDAP signal reached the target electrode in the shortest time (~250 ms), while DC signal took a longer time (~300 ms) and AC signal takes the longest time (~400 ms) to complete the droplet transportation.

A droplet running across an 8-electrode straight array was monitored to obtain the average velocity driven by DC, AC or NDAP. The charging duration of DC and AC was empirically optimized at 300 ms and 400 ms, respectively, to complete a movement from one electrode to the next. The average velocity was calculated in the droplet movement disregarding whether the actuation signal stopped or not.

Figure 5B:
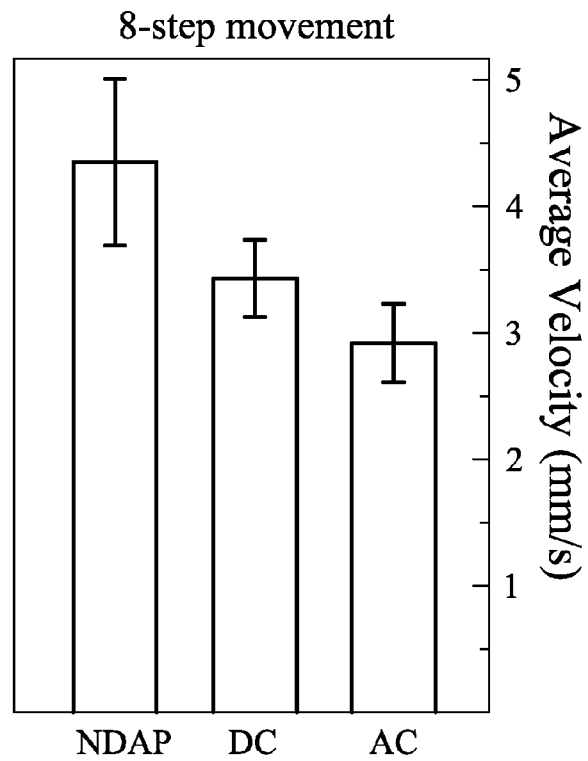
FIG. 5B is a diagram showing average velocity of a droplet moving across an eight-electrode straight array according to FIG. 5A.

FIG. 5B is a diagram showing average velocity of a droplet moving across an eight-electrode straight array according to FIG. 5A. As shown in FIG. 5B, NDAP reached a velocity of 4.4 mm/s while DC gave 3.4 mm/s and AC only reached 2.9 mm/s. NDAP enhanced the velocity by 26.8% and 49.5% when compared to DC and AC, respectively. According to the dielectric dispersion, the dielectric permittivity decreases as a function of frequency of the applied electric field. Consequently, the EWOD force induced by the DC electric field can be higher than that of AC, as well as the actuation velocity. Generally, the DC-based actuation signal would give higher transportation efficiency.

Figure 6A:
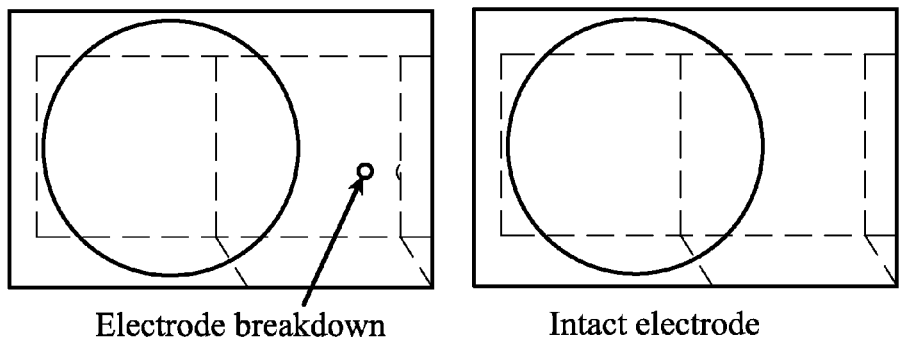
FIG. 6A is a schematic showing an intact electrode and a break down electrode according to one embodiment of the present disclosure.
Figure 6B:
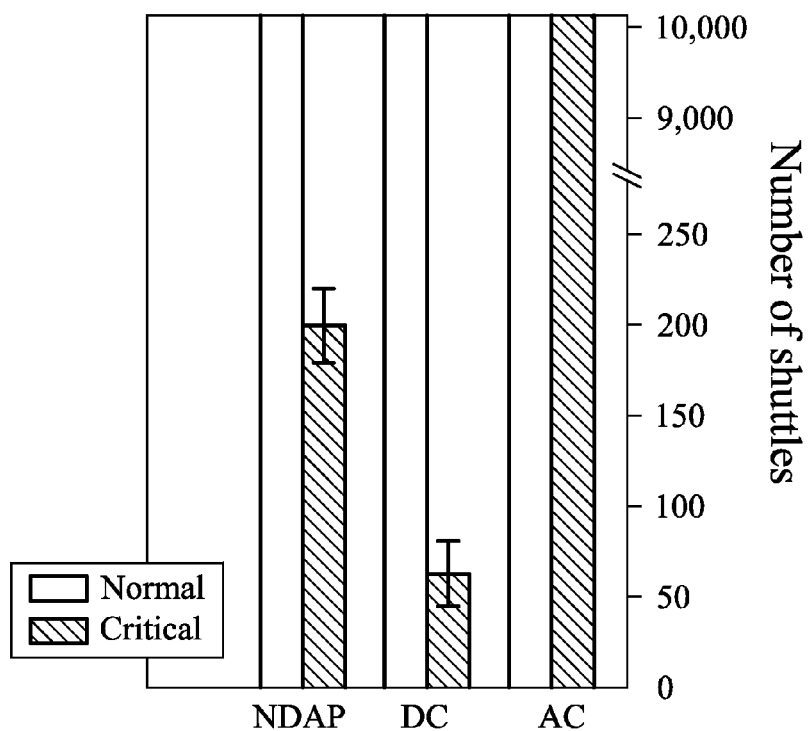
FIG. 6B is a diagram showing number of shuttles of a droplet being completed before electrode breakdown according to one embodiment of the present disclosure.

Since NDAP has low RMS voltage we expected that the electrode lifetime with NDAP would be longer than both DC and AC. To test this hypothesis we shuttled a droplet between two adjacent electrodes driven by DC, AC and NDAP. The charging duration of DC and AC was set empirically at 250 ms and 400 ms. The electrode lifetime was determined when an electrode breakdown was monitored (FIG. 6A), although the droplet could still move in some cases. The dielectric layer was normally 250 nm in the experiments in this paper. As shown in FIG. 6B, the electrode did not show any sign of breakdown after 10,000 shuttles for all the three actuation signals at normal dielectric coating conditions.

In order to touch the limit of electrode lifetime, we coated a batch of EWOD device with critical thickness of 50 nm of dielectric layer which are prone to breakdown. As shown in FIG. 6B, NDAP had an electrode lifetime about 3 times longer than that of DC with a value of 200 and 63 shuttles, respectively. This would be due to the lower RMS value of NDAP. But unexpectedly, EWOD device actuated by AC were still robust even under those critical coating conditions. We suspect this may be attributed to the defects or impurities in the thin layer of dielectric material. For dielectric layer as thin as 50 nm, the number of defects and impurities dramatically increase, which causes charge trapping. According to Poole-Frenkel emission conduction mechanism, the trapped electrons can escape by thermal emission, and form current due to electrons 'jumping' from trap to trap. It was found that the charge trapping related leakage current is more obvious for DC-based signal than AC, resulting in a field stress in DC and NDAP and the lowering of the electrode lifetime.

However, in the DMF system, prior arts always coat a EWOD device with thick enough dielectric layer for a robust performance. Therefore, the lifetime of all the three actuation signals is same good in real usage. Nevertheless, under some circumstances when the droplet contained charged materials such as protein or DNA, DC based signals with the same polarity of charge as the sample would be desired, in order to eliminate the adhesion of those materials to the electrodes. In those cases, NDAP would be preferable in the view of both velocity and electrode lifetime.

Figure 7A:
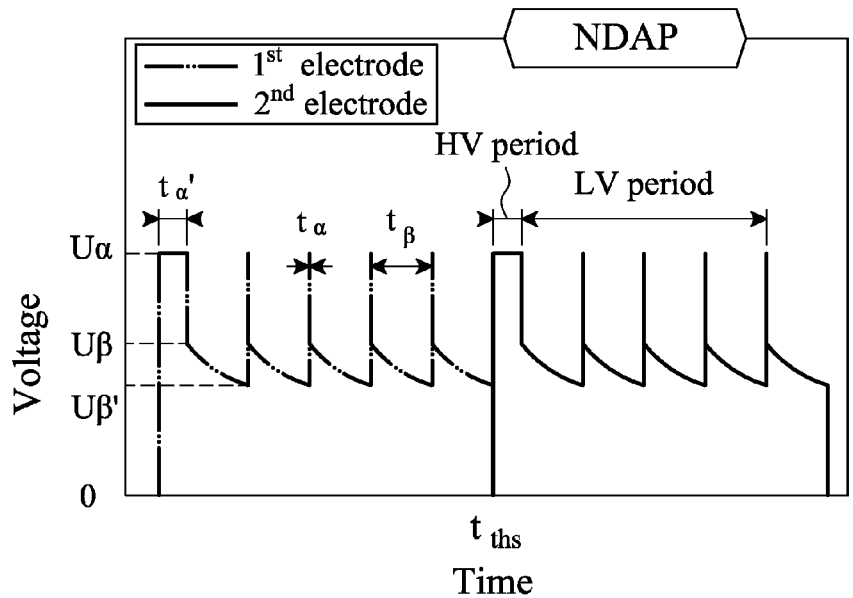
FIGS. 7A-7D are diagrams showing four electrode-driving schemes for droplet movements over two electrodes according to one embodiment of the present disclosure.
Figure 7B:
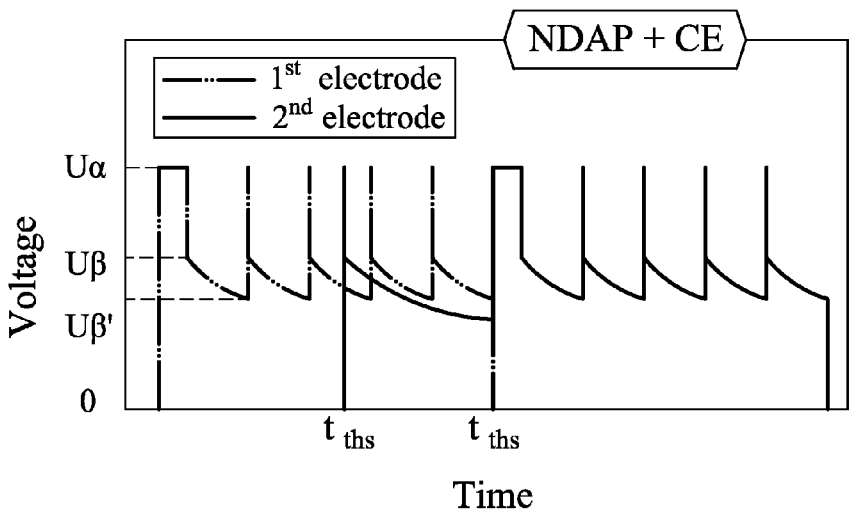
Figure 7C:
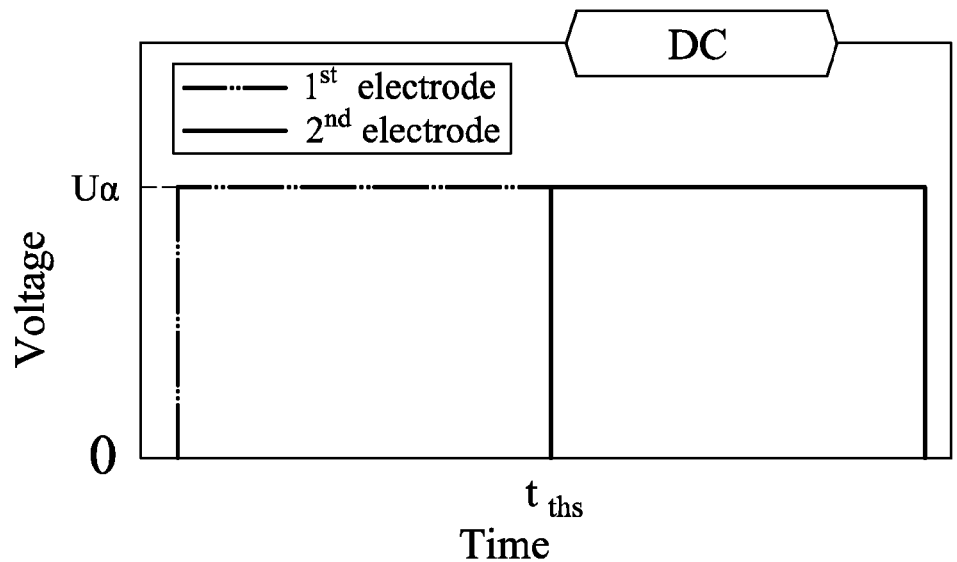
Figure 7D:
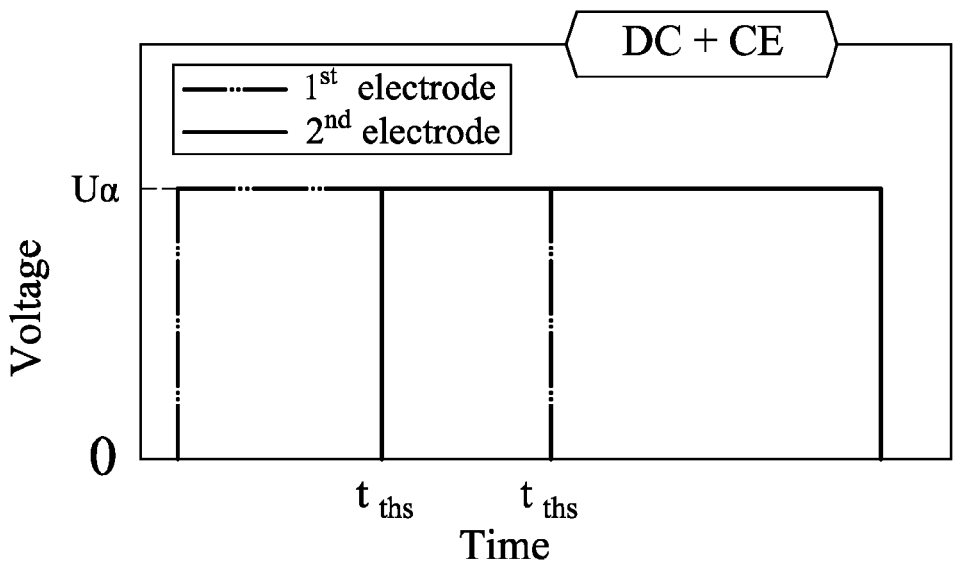
Figure 7E:
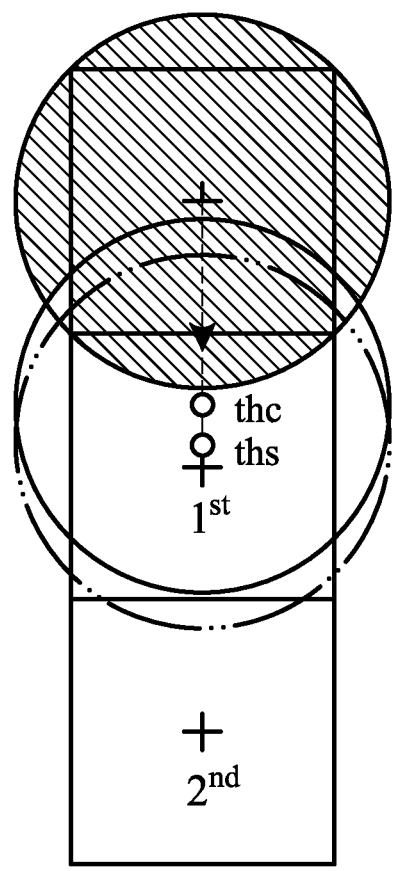
FIG. 7E is a sketch showing droplet moving toward two target electrodes and location of two thresholds on the first target electrode according to one embodiment of the present disclosure.

Another electrode-driving technique of present disclosure is Cooperative Electrodes (CE). CE is inspired by the fact that when a droplet is transported over a sequence of electrodes, the droplet suffers from deformation and local vibration, lowering the average $v_{droplet}$ between the gap of the electrodes. In fact, the next target electrode can be early-charged before discharging the current one to regulate $v_{droplet}$ over a sequence of electrodes transportation. Guided by the real-time droplet position feedback, the electrodes overlap charging time can be optimally calculated by the software engine, with no extra cost. Also, CE is independent of the actuation waveform. FIGS. 7A and 7B illustrate the cases of NDAP and NDAP+CE, whereas FIGS. 7C and 7D depict the cases of simple DC and DC+CE, respectively. Two crucial timing $t_{ths}$ and $t_{thc}$, are defined as: the leading edge of the droplet to reach the next electrode, and the droplet's center to overlap with that of the target electrode, respectively. For NDAP+CE, the charging is specialized to pulse the second electrode after $t_{ths}$. For DC+CE, the charging of the two adjacent electrodes was overlapped. CE should be started right on time, requiring a feedback to track the droplet position in real time and perform self-optimization. The CE is triggered when the monitored position reaches the predefined thresholds $t_{ths}$ and $t_{thc}$ as shown in FIG. 7E.

Figure 8:
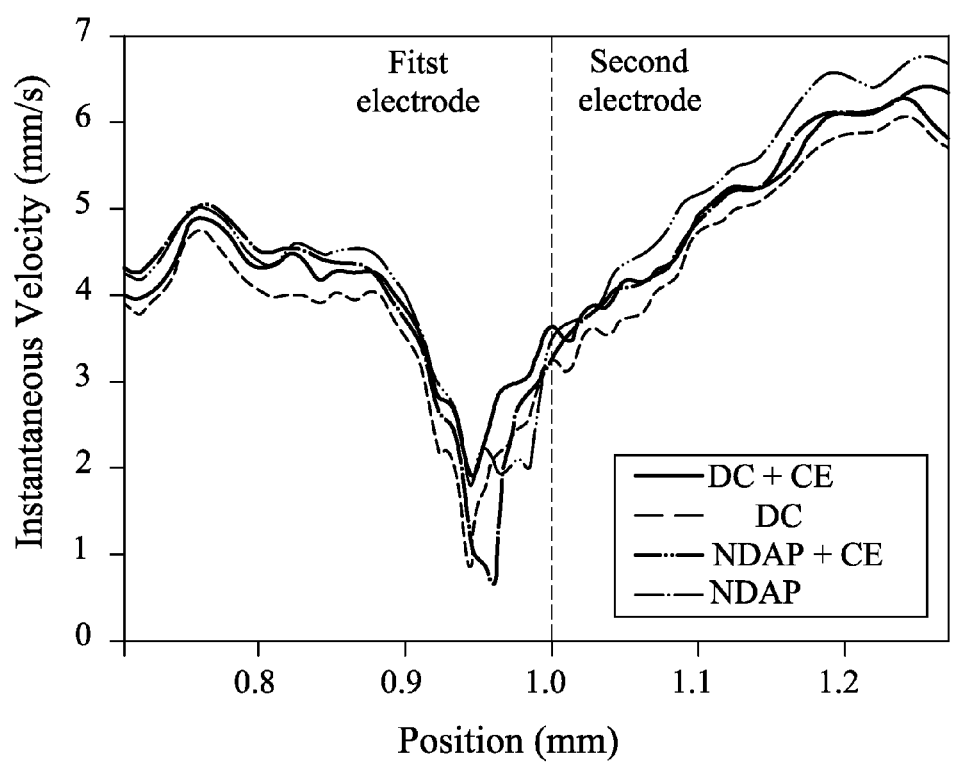
FIG. 8 is a diagram showing comparison between individual and cooperative electrode-driving techniques in terms of transportation velocity according to one embodiment of the present disclosure.

Conventionally, when a droplet is transported over a row of electrodes, only one individual electrode is charged. It had been observed that $v_{droplet}$ decelerated significantly when the center of a droplet approached that of the electrode, being a main factor limiting the average $v_{droplet}$. When we cooperatively charged two adjacent electrodes (CE), the deceleration phenomenon was greatly inhibited. FIG. 8 shows the velocity of NDAP (13 ms, $t'_\alpha$) and DC enhanced by CE. Obviously, at ~0.95 mm, the minimum $v_{droplet}$ under CE was higher than that without enhancement. The same improvement can be seen on the DC case as well.

Figure 9A:
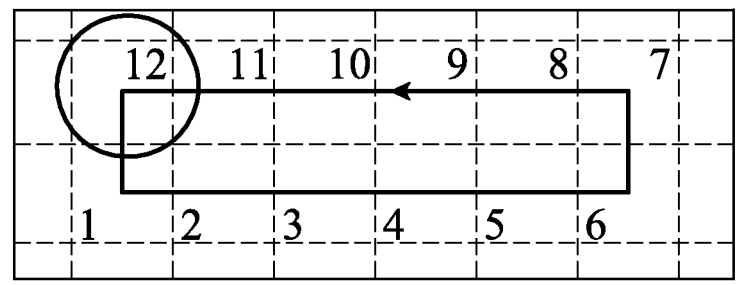
FIG. 9A is an image showing whole droplet transportation driving by NDAP+CE according to one embodiment of the present disclosure.
Figure 9B:
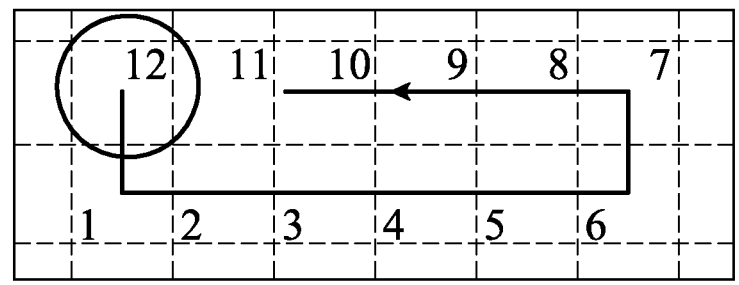
FIG. 9B is an image showing whole droplet transportation driving by DC.

As shown above NDAP+CE had dramatically improved the transportation characteristics of a droplet between two adjacent electrodes compared with that driven by DC. A droplet moving across 12 electrodes arranged by a 2×6 matrix driven by either NDAP+CE or DC only was monitored and studied. The traces of the centroids of the moving droplet are shown in FIGS. 9A and 9B. It shows that when more electrodes were involved with the same running conditions, the enhancement was indeed more obvious. The DC signal charging time was fixed empirically at 260 ms (just adequate to transport the droplet to the next electrode) and $t'_\alpha$ of NDAP was 13 ms. The whole running time was set at 3 s such that the droplet driven by NDAP+CE could complete a whole travel and return to the origin. However, during the same charging period, the droplet driven by DC only completed 10 electrodes. The average time for the droplet to move across single electrode for NDAP+CE and DC signals were 223 and 260 ms, with average velocities of 4.48 and 3.84 mm/s, respectively.

Figure 9C:
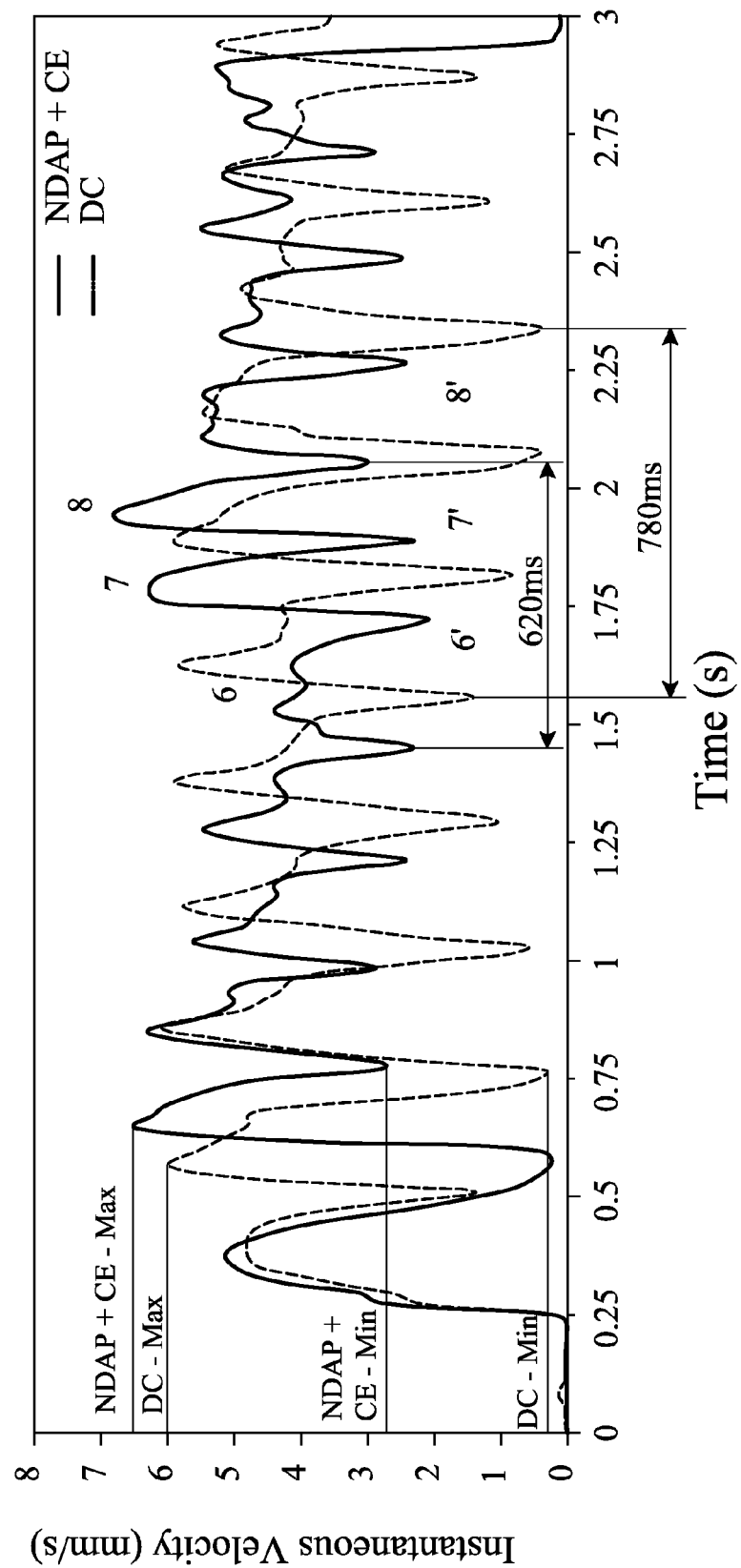
FIG. 9C is a diagram showing instantaneous velocity of droplet moving across the electrodes according to FIGS. 9A-9B.

FIG. 9C is a diagram showing instantaneous velocity of droplet moving across the electrodes according to FIGS. 9A-9B. It can be seen that NDAP+CE dramatically and reliably reduced the decrease of velocity between two adjacent electrodes. The velocity of NDAP+CE at electrode No. 6 was smaller than that of DC. Moreover, the total time of getting through the corner (No. 6, 7 and 8) was much shorter (620 ms) than that of DC (780 ms). The direction change toward electrode No. 7 of NDAP+CE was also earlier than DC. This curved movement could be very useful in terms of quickly mixing/circulating of droplets on EWOD device.

Figure 9D:
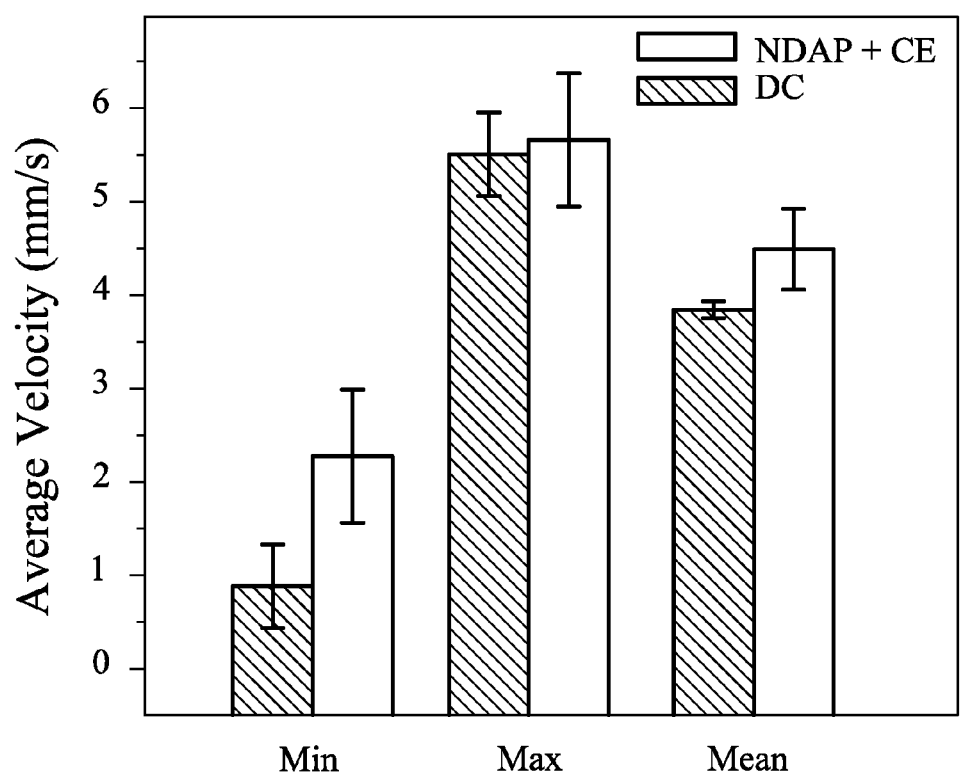
FIG. 9D is a diagram showing average velocities of minimum/maximum instantaneous velocities and mean velocities across each electrode.

As shown in FIG. 9C, when a droplet moves along an electrode, the velocity is not constant. It vibrates across each electrode. We analyzed the velocities in groups as maximum, minimum and in average to find out which part NDAP+CE significantly enhanced to improve its overall transportation efficiency. FIG. 9D is a diagram showing average velocities of minimum/maximum instantaneous velocities and mean velocities across each electrode. As shown in FIG. 9D, the minimum velocities were greatly enhanced by 2.5 times by NDAP+CE while the maximum velocities are comparable between NDAP+CE and DC. This causes an overall increase in the average velocity of 16.6% by NDAP+CE. The significance of the data had been tested ($p<0.01$).

Raising the DC voltage could greatly improve the droplet transportation velocity. As a DC based manageable pulse actuation, NDAP can be used at any voltage. In another word, no matter what DC voltage is used to improve the droplet transportation, switching to NDAP+CE would gain another 15% over the enhancement. Especially for a high DC voltage, NDAP+CE would be more preferred for its low RMS value has less possibility in shortening the lifetime of the electrode due to dielectric breakdown.

In summary, present disclosure has introduced two electrode-driving techniques, Natural Discharge after Pulse (NDAP) and Cooperative Electrodes (CE), with a real time feedback control in DMF system and speeded up the droplet movement beyond those achieved by conventional actuation signal via matching the droplet dynamics with the strength and duration of the applied electric field. The entire scheme involves only low-cost electronics and software programming. That gives the feasibility to be upgraded for further researches, customized to other applications, and easily repeated by others.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A digital microfluidic system, comprising:
    a device including a droplet on an electrode array, wherein the electrode array includes a plurality of electrodes;
    a control electronics connecting to the device and providing an actuation pulse to the electrodes, wherein the control electronics generates a capacitance-derived frequency signal;
    a field programmed gate array (FPGA) connecting to the control electronics and collecting the capacitance-derived frequency signal; and
    a computer connecting to the FPGA, the computer using a frequency of the capacitance-derived frequency signal to calculate a precise droplet position and generating a duration voltage signal;
    wherein the control electronics includes a printed circuit board (PCB) having a high-voltage (HV) switches IC chip array, a blocking capacitance array, an analog switches IC chip array, and a ring oscillator.

2. The digital microfluidic system of claim 1, wherein the device is an electrowetting-on-dielectric (EWOD) device.

3. The digital microfluidic system of claim 2, wherein the EWOD device comprises:
    a first plate;
    a second plate facing the first plate; and
    the droplet in between the first plate and the second plate;
    wherein the electrode array is on the second plate.

4. The digital microfluidic system of claim 2, wherein the EWOD device further comprises a gap between the first plate and the second plate, wherein the gap is in the range of 1 µm to 1000 µm.

5. The digital microfluidic system of claim 1, wherein the HV switches IC chip array is for connecting/disconnecting the actuation pulse to the electrodes.

6. The digital microfluidic system of claim 1, wherein the ring oscillator is for generating the capacitance-derived frequency signal.

7. The digital microfluidic system of claim 1, wherein the analog switches IC chip array is for connecting/disconnecting the electrodes to the ring oscillator.

8. The digital microfluidic system of claim 1, wherein the blocking capacitance array is for connecting electrodes to the analog switches array, and for blocking a HV signal from the actuation pulse to the analog switches array.

9. The digital microfluidic system of claim 1, wherein the electrodes are coplanar.

10. A digital microfluidic system, comprising:
   a device including a droplet and an electrode array, wherein the electrode array includes a first electrode and a second electrode;
   a control electronics connecting to the device and providing a first pulse to the first electrode, wherein the control electronics generates a capacitance-derived frequency signal;
   a field programmed gate array (FPGA) connecting to the control electronics, and collecting the capacitance-derived frequency signal; and
   a computer connecting to the FPGA, the computer using a frequency of the capacitance-derived frequency signal to calculate a precise droplet position and generating a duration voltage signal;
   wherein the control electronics conducts a control process according to the duration voltage signal, the control process including:
      providing the first pulse to the first electrode for kicking off the droplet till a centroid of the droplet reaching a centroid of the first electrode; and
      providing a second pulse to the second electrode when a leading edge of the droplet reaches the second electrode; and
      wherein the control electronics includes a printed circuit board (PCB) having a high-voltage (HV) switches IC chip array, a blocking capacitance array, an analog switches IC chip array, and a ring oscillator.

11. The digital microfluidic system of claim 10, wherein the device is an electrowetting-on-dielectric (EWOD) device.

12. The digital microfluidic system of claim 11, wherein the EWOD device comprises:
   a first plate;
   a second plate facing the first plate; and
   the droplet in between the first plate and the second plate;
   wherein the electrode array is on the second plate.

13. The digital microfluidic system of claim 12, wherein the EWOD device further comprises a gap between the first plate and the second plate, wherein the gap is in the range of 1 μm to 1000 μm.

14. The digital microfluidic system of claim 10, wherein the electrodes are coplanar.

* * * * *